United States Patent [19]

Wasicek et al.

[11] Patent Number: 5,507,301

[45] Date of Patent: Apr. 16, 1996

[54] CATHETER AND GUIDEWIRE SYSTEM WITH FLEXIBLE DISTAL PORTIONS

[75] Inventors: Lawrence D. Wasicek, Sunnyvale; Dennis L. Brooks, Santa Clara, both of Calif.

[73] Assignee: Advanced Cardiovascular Systems, Inc., Santa Clara, Calif.

[21] Appl. No.: 365,324

[22] Filed: Dec. 28, 1994

Related U.S. Application Data

[63] Continuation of Ser. No. 155,952, Nov. 19, 1993, abandoned.

[51] Int. Cl.⁶ .................................. A61B 5/00; A61M 29/00
[52] U.S. Cl. ........................... 128/772; 604/96; 606/192
[58] Field of Search .......................... 604/96–103, 170; 606/192–196; 128/772, 656–658

[56] References Cited

U.S. PATENT DOCUMENTS

| | | | |
|---|---|---|---|
| 4,538,622 | 9/1985 | Samson et al. | 128/772 |
| 4,616,653 | 10/1986 | Samson et al. | 604/95 X |
| 4,619,274 | 10/1986 | Morrison et al. | 128/772 |
| 4,721,117 | 1/1988 | Mar et al. | 128/772 |
| 4,748,986 | 6/1988 | Morrison et al. | 128/772 |
| 4,867,173 | 9/1989 | Leoni | 128/772 |
| 4,921,483 | 5/1990 | Wijay et al. | 604/96 |
| 4,976,720 | 12/1990 | Machold et al. | 606/194 |
| 5,047,045 | 9/1991 | Arney et al. | 606/194 |
| 5,069,217 | 12/1991 | Fleischhacker, Jr. | 128/657 |
| 5,144,959 | 9/1992 | Gambale et al. | 128/772 |
| 5,209,730 | 5/1993 | Sullivan | 604/96 |
| 5,243,996 | 9/1993 | Hall | 128/772 |
| 5,338,295 | 8/1994 | Cornelius et al. | 604/96 |

*Primary Examiner*—John D. Yasko
*Assistant Examiner*—Adam J. Cermak
*Attorney, Agent, or Firm*—Crosby, Heafey, Roach & May

[57] ABSTRACT

A guidewire having a core member with proximal, intermediate and distal sections and a flexible coil on the distal section and a catheter assembly or kit with such guidewire. The proximal section of the core may be substantially longer than the combined lengths of both the intermediate and distal sections and has a diameter which is at least 0.001 inch greater than the diameter of the intermediate section. The intermediate section has a diameter which is at least 0.002 inch greater than the diameter of the distal section. Improved pushability and a greater flexibility in the distal and intermediate sections are obtained. A catheter which is used with the guidewire has a proximal section of about 100 cm and a distal section of at least about 15 cm in length and an inner lumen having diameter of at least 0.003 inch less than the inner diameter of the inner lumen in the proximal section.

23 Claims, 1 Drawing Sheet

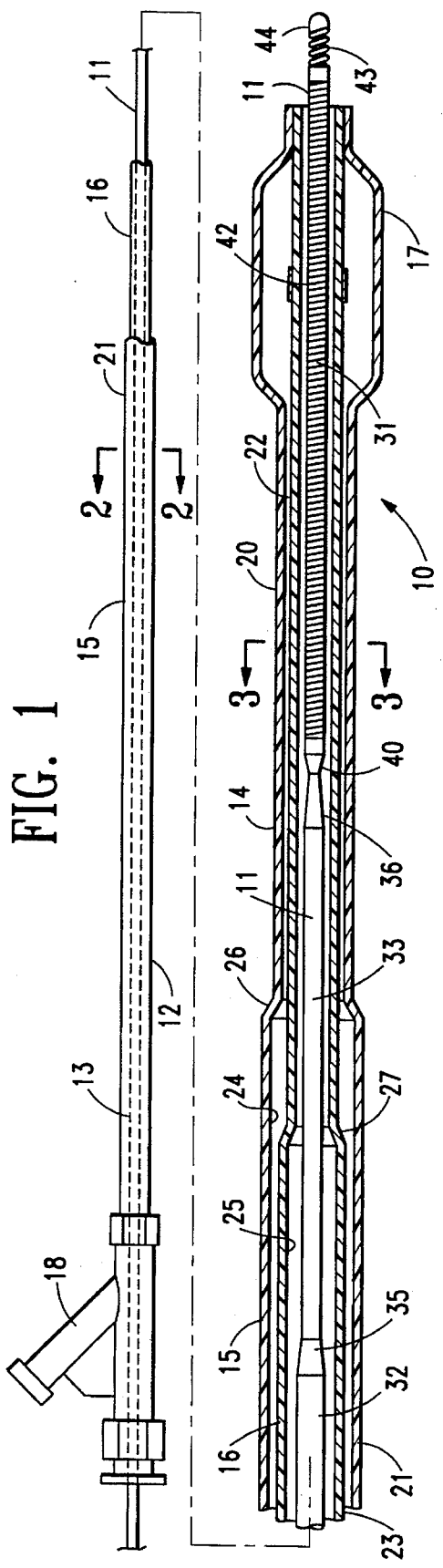
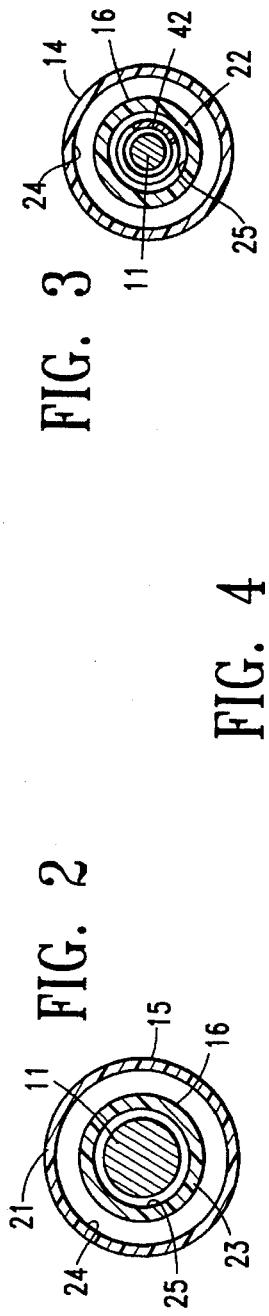
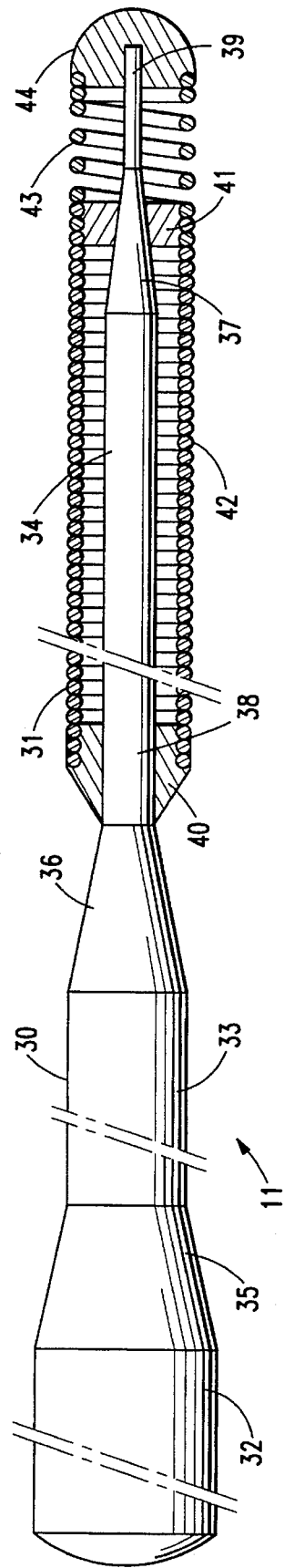
FIG. 1
FIG. 2
FIG. 3
FIG. 4

CATHETER AND GUIDEWIRE SYSTEM WITH FLEXIBLE DISTAL PORTIONS

This is a continuation of application Ser. No. 08/155,952 filed on Nov. 19, 1993, entitled CATHETER AND GUIDEWIRE SYSTEM WITH FLEXIBLE DISTAL PORTIONS (now abandoned).

BACKGROUND OF THE INVENTION

This invention relates to the field of medical devices, and more particularly to a guidewire for advancing a catheter within a body lumen in a procedure such as percutaneous transluminal coronary angioplasty (PTCA).

In a typical PTCA procedure a guiding catheter having a preformed distal tip is percutaneously introduced into the cardiovascular system of a patient by means of a conventional Seldinger technique and advanced therein until the distal portion of the guiding catheter is located within the patient's ascending aorta with distal tip of the guiding catheter seated in the ostium of a desired coronary artery. A guidewire is positioned within an inner lumen of an over-the-wire dilatation catheter and then both are advanced through the guiding catheter to its distal end. The guidewire is first advanced out of the distal end of the guiding catheter into the patient's coronary vasculature until the distal end of the guidewire crosses a lesion to be dilated. Then the dilatation catheter, having an inflatable balloon on the distal portion thereof, is advanced into the patient's coronary anatomy over the previously introduced guidewire until the balloon of the dilatation catheter is properly positioned across the lesion. Once in position across the lesion, the balloon is inflated one or more times to a predetermined size with liquid at relatively high pressures (e.g. greater than 4 atmospheres) to compress the arteriosclerotic plaque of the lesion against the inside of the artery wall and to otherwise expand the inner lumen of the artery. Generally, the inflated diameter of the balloon is approximately the same as the natural diameter of the body lumen being dilated. Inflation to a diameter smaller than the natural diameter will result in and incomplete dilatation and inflation to a diameter larger than the natural diameter can result in damage to the arterial wall. After the balloon is finally deflated, blood flow resumes through the dilated artery and the dilatation catheter can be removed therefrom.

The lesion or lesions to be dilated within the patient's coronary artery may be located from a few centimeters up to about 20 cm or more from the distal end of the guiding catheter which is seated in the patient's coronary ostium. This requires the guidewire to be extendable for up to 25 cm or more from the distal end of the guiding catheter because the distal end of the guidewire must extend well beyond the lesion to be dilated so that the dilatation balloon on the distal end of the catheter can be properly positioned within the stenotic region.

Conventional guidewires for angioplasty and other vascular procedures usually comprise an elongated core member with one or more smaller diameter sections near the distal end thereof and a flexible body such as a helical coil disposed about the distal portion of the core member. A shapable member, which may be the distal extremity of the core member or a separate shaping ribbon secured to the distal extremity of the core member, extends through the flexible body and is secured to a rounded plug at the distal end of the flexible body. Torquing means are provided on the proximal end of the core member to rotate, and thereby steer, the guidewire while it is being advanced through a patient's vascular system.

A major requirement for guidewires and other guiding members, whether they be solid wire or tubular members, is that they have sufficient column strength to be pushed through a patient's vascular system or other body lumen without kinking. However, the distal section of the guidewire must be flexible enough to avoid damaging the blood vessel or other body lumen through which it is advanced. Efforts have been made to improve both the strength and flexibility of guidewires to make them more suitable for their intended uses, but these two properties tend to be diametrically opposed to one another, in that an increase in one usually involves a decrease in the other. There has been a gradual decrease in the profiles or transverse dimensions of commercially available intravascular catheters and guidewires particularly for use in coronary arteries. However, concomitant with the decrease in profile has been a loss in pushability. Stiffening members have been employed with catheters but they have complicated the procedures of use, because the stiffening member usually would have to be removed from an inner lumen of the catheter in order for the inner lumen to be utilized, e.g. for inflating the balloon or advancing a guidewire therethrough. Stiffening members have also increased the complexity of the manufacturing process for dilatation catheters.

What has been needed and heretofore unavailable is a guidewire which is particularly suitable for use in an over-the-wire dilatation catheter system with a very flexible distal portion to facilitate advancement within a patient's coronary anatomy and a proximal portion with greater pushability. The present invention provides a guidewire and a dilatation catheter system including the guidewire which provides such a desirable combination of such properties.

SUMMARY OF THE INVENTION

The present invention is directed to a guidewire, and a combination of an over-the-wire dilatation catheter system with such a guidewire, which has improved pushability and distal flexibility.

The guidewire of the invention is configured to be advanced through a patient's vasculature and into a coronary artery thereof. It is provided with an elongated core member having a proximal core section with a relatively large outer diameter, an intermediate core section with an intermediate sized outer diameter and a distal core section with a relatively small outer diameter. The length of the proximal section is at least about 40 cm, preferably about 100 to about 140 cm, and the outer diameter is about 0.010 to about 0.035 inch (0.254–0.89 mm). The intermediate core section has a length of at least 3 cm up to about 100 cm, preferably about 15 to about 30 cm and an outer diameter of at least 0.001 inch (0.025 mm) less than the minimum outer diameter of the proximal core section. The distal core section has a length of at least about 3 cm, preferably about 15 to about 35 cm, and an outer diameter of at least 0.002 inch less than the minimum outer diameter of the intermediate section. The total length of the guidewire is preferably about 150 to about 200 cm, e.g. 175 cm which is typical for commercially available guidewires for angioplasty and other coronary artery procedures but it may be as long as 300 cm to allow for catheter exchange. Tapered transition regions about 2 to about 6 cm in length extend between the proximal and intermediate core sections and between the intermediate and distal core sections.

A flexible member, such as a helical coil, is disposed about at least a portion of the distal core section and has an outer diameter varying by not more than about 0.0015 inch (0.381 mm) from the outer diameter of the intermediate core section. The diameter of the wire forming the coil is about 0.001 to about 0.003 inch (0.0254–0.076 mm).

The dilatation catheter of the invention is provided with a catheter shaft having an overall length shorter than the overall length of the guidewire. The catheter shaft has a proximal section with a length of at least about 90 to about 120 cm and a distal section with a length of about 15 to about 30 cm with the total length of the catheter shaft being about 120 to about 150 cm. At least the distal section of the catheter shaft preferably includes an inner tubular member and an outer tubular member disposed about the inner tubular member. A first inner lumen, which is adapted to slidably receive a guidewire, extends through the catheter shaft with the portion of the first inner lumen within the proximal catheter shaft section having a diameter which is at least 0.002 inch (0.051 mm) greater than the diameter of the inner lumen extending within the distal catheter shaft section.

In one presently preferred embodiment, essentially the entire catheter shaft is formed of an inner tubular member and an outer tubular member. The first inner lumen extends within the inner tubular member and a second inner lumen extends between the inner and outer tubular members and is adapted to direct inflation fluid from the proximal end of the catheter to the interior of a dilatation balloon on the distal section of the catheter shaft. The inner tubular member has a proximal portion with a length less than the length of the proximal portion of the outer tubular member but in no event less than about 90 cm. The distal portion of the inner tubular member has a length which is greater than the length of the distal portion of the outer tubular member and in no event less than 20 cm. The inner tubular member is provided with a guidewire receiving inner lumen extending therein with a diameter of about 0.01 to about 0.022 inch (0.254–0.559 mm) in the proximal portion thereof and about 0.008 to about 0.015 inch (0.203–0.381 mm) in the distal portion thereof, with the inner lumen in the proximal portion being at least 0.002 inch greater than the inner lumen within the distal portion. Preferably, the diameter of the inner lumen within the distal portion of the inner tubular member is slightly larger than the outer diameter of the proximal section of any guidewire which is to be disposed within the inner lumen so as to allow some movement of the proximal section of the guidewire into the distal portion of the inner tubular member. Tapered transitions may be provided between the proximal and distal portions of the inner and outer tubular members of the dilatation catheters.

An inflatable dilatation member or balloon is provided on the distal section of the catheter shaft having an interior in fluid communication with an inflation lumen extending between the inner and the outer tubular members.

The relatively large diameter proximal core section, which can extend most of the length of the guidewire, provides substantial pushability to the guidewire and the short intermediate and distal core sections and provide increased flexibility and ease in handling. The combined lengths of the intermediate and distal core sections are sufficient to ensure that the small diameter distal tip of the guidewire can be advanced well beyond the stenosis to be dilated. These and other advantages of the invention will become more apparent from the following detailed description and the accompanying exemplary drawings.

BRIEF DESCRIPTION OF THE DRAWINGS

FIG. 1 is an elevational view partially in section of a dilatation catheter assembly with a guidewire therein which embodies features of the invention.

FIG. 2 is a transverse cross-sectional view of the catheter assembly shown in FIG. 1 taken along the lines 2—2.

FIG. 3 is a transverse cross-sectional view of the catheter assembly shown in FIG. 1 taken along the lines 3—3.

FIG. 4 is an enlarged elevational view partially in section of the distal portion of the guidewire shown in FIG. 1.

DETAILED DESCRIPTION OF THE INVENTION

Reference is made to FIGS. 1–3 which depict a dilatation catheter assembly embodying features of the invention which includes a dilatation catheter 10 and a guidewire 11. The dilatation catheter 10 has an elongated catheter shaft 12 with proximal and distal sections 13 and 14. The shaft 12 includes an outer tubular member 15 and an inner tubular member 16 which is disposed within the outer tubular member, an inflatable dilatation member 17, and an adapter 18 which is secured to the proximal end of the catheter shaft 12. The outer tubular member 15 has a relatively short distal section 20 and a relatively long proximal section 21 which has inner and outer diameters larger than the inner and outer diameters of the distal section. The inner tubular member 16 has a relatively short distal section 22 and a relatively long proximal section 23, the latter having inner and outer diameters larger than the inner and outer diameters of the distal section. An annular lumen 24 extends between the inner tubular member 16 and the outer tubular member 15 and is adapted to direct inflation fluid from the adapter 18 to the interior of the inflatable dilatation member 15 for the inflation thereof. The inner tubular member 14 is provided with an inner lumen 25 which is adapted to slidably receive guidewire 11. The lengths of the proximal and distal sections of the outer tubular member generally correspond to the lengths of the proximal and distal sections of the catheter shaft previously discussed. The inner diameter of the outer tubular member 15 ranges from about 0.002 to about 0.004 inch (0.051–0.102 mm) greater than the outer diameter of the inner tubular member 16. The proximal section of the inner tubular member 16 has a length of about 1 to about 10 cm less than the length of the proximal section of the outer tubular member 15 and diameter of the inner lumen extending within the proximal section is about 0.012 to about 0.022 inch. Tapered transition sections 26 and 27 are provided between the proximal and distal sections of the outer and inner tubular members 15 and 16 respectively. The wall thickness of the inner and outer tubular members along their lengths depends upon the strength of the material from which the tubular member is made, the higher strength materials allowing for much thinner walled structures. In this regard, the inner and outer tubular members can be formed of a variety of well known polymeric and metallic materials which have been similarly used. Suitable polymeric materials include polyethylene, polyamide, polyvinyl chloride and polyesters such as commercially available Hytrel®. Suitable metallic materials include NiTi type alloys having shape memory/pseudoelastic characteristics at body temperature.

The guidewire 11, as shown more clearly in FIG. 4, generally comprises an elongated core member 30 and a flexible coil 31. The core member 30 has three sections, a proximal core section 32, and an intermediate core section 33 and a distal core section 34. A first tapered transition core section 35 extends between the proximal core section 32 and the intermediate core section 33 and a second tapered transition core section 36 extends between the intermediate core section and the distal core section 34. A third transition core section 37 may be provided between the cylindrical portion 38 of the distal core section 34 and a flattened shapable ribbon 39 which has a generally rectangularly shaped transverse cross-section about 0.0005 to about 0.002 inch (0.013–0.051 mm) in short transverse dimensions and about 0.0008 to about 0.005 inch (0.02–0.127 mm) in the long transverse dimensions. The core member 30 can be formed of stainless steel or NiTi type alloys having shape memory/pseudoelastic characteristics at body temperature.

The coil 31 is secured to the core member 30 at the coil's proximal end by means of solder or brazement 40 and at an intermediate location by means of solder or brazement 41. The coil 31 is preferably provided with a proximal coil section 42 and a distal coil section 43 which is substantially more radiopaque than the proximal coil section. The proximal end of the distal coil section 43 and the distal end of the proximal coil section 42 are interthreaded and joined at the intermediate location by solder or brazement 41 to the core member 30 at the tapered transition 37. The preferred joint is formed with a solder containing about 95% tin and 5% silver. The flattened, rectangularly shaped distal end of the core member 30 is bonded to the distal end of the coil 31 by means of a soldered joint which forms the rounded plug 44. The outer diameter of the coil 31 is about 0.008 to about 0.012 inch (0.203–0.305 mm) and is preferably at most just slightly larger than the outer diameter of the intermediate core section 33 to ensure easy passage through the inner lumen 25 in the distal section 22 of the inner tubular member 16. The coil 31 is preferably formed from wires about 0.0015 to about 0.003 inch (0.038–0.076 mm) in diameter. The proximal coil section 42 is preferably made from stainless steel and the distal coil section 43 is made from a highly radiopaque material such as titanium, platinum, palladium or palladium alloys with indium or rhenium which are well know to those skilled in the art. The distal coil section 43 is preferably expanded so that two or more of the turns do not contact in order to provide a greater degree of flexibility to the distal tip of the guidewire.

In an alternative embodiment, the guidewire 11 may be provided with a conventional floppy distal construction wherein the core member terminates short of the distal end of the coil member and a separate, relatively short, manually shapable ribbon extends to the distal end of the coil and is joined to the distal end by the plug on the distal end of the coil. The distal tip of the core member is provided with a rounded shape to prevent it from extending through the coil and possibly causing damage to the surrounding arterial wall of the patient. A mandrel (not shown) may be disposed within the annular lumen between the inner and outer tubular member to provide additional stiffness.

The use of the guidewire of the invention, and the dilatation catheter assembly with the guidewire of the invention, for the most part follows conventional angioplasty procedures. However, there are notable differences. The relatively large diameter proximal core section of the guidewire provides excellent pushability to the guidewire to facilitate its advancement through the guiding catheter and coronary anatomy and excellent handling, whereas the relatively small diameter intermediate and distal core sections provide increased flexibility allowing the distal portion of the guidewire to readily flex as it passes through tortuous coronary arteries.

Those skilled in the art will recognize that the invention has been described herein in terms of certain preferred embodiments and that various modifications can be made to the invention without departing from the scope thereof.

What is claimed is:

1. A guidewire configured for advancement within a patient's coronary artery comprising:
   a) a core member which includes
      an elongated proximal core section;
      an intermediate core section having a diameter of at least about 0.001 inch less than the diameter of the proximal section, and
      a distal core section having a diameter of at least 0.002 inch less than the diameter of the intermediate section; and
   b) a flexible member disposed about the distal core section and having an outer diameter not more than about 0.0015 inch greater than the diameter of the intermediate core section.

2. The guidewire of claim 1 wherein the proximal core section has a length of at least 100 cm and a diameter between about 0.01 and about 0.02 inch.

3. The guidewire of claim 1 wherein the intermediate core section has a length of at least 3 cm.

4. The guidewire of claim 1 wherein the distal core section has a length of at least 3 cm.

5. The guidewire of claim 1 wherein the distal core section has a flattened distal tip.

6. The guidewire of claim 1 wherein the flexible member is a helical coil.

7. The guidewire of claim 5 wherein the helical coil has a plurality of longitudinally expanded turns in a distal portion.

8. The guidewire of claim 6 wherein the helical coil has a distal portion which is more highly radiopaque than a proximal portion of the coil.

9. The guidewire of claim 1 wherein the individual lengths of the intermediate and distal core sections are about 15 to about 30 cm.

10. The guidewire of claim 1 wherein the length of the proximal core section is at least 40 cm.

11. The guidewire of claim 1 wherein a tapered transition section is provided between the proximal core section and the intermediate core section.

12. The guidewire of claim 1 wherein a tapered transition section is provided between the intermediate core section and the distal core section.

13. The guidewire of claim 1 wherein the intermediate core section has a length of at least 10 cm.

14. The guidewire of claim 1 wherein the distal core section has a length of at least 10 cm.

15. An over-the-wire dilatation catheter comprising:
   a) an outer tubular member having a relatively long proximal section with an inner lumen extending therein and a relatively short distal section with an inner lumen extending therein, with the inner lumen within the distal section having a diameter less than the diameter of the inner lumen within the proximal section;
   b) an inner tubular member with a proximal section having a length less than the length of the proximal section of the outer tubular member, a distal section with a length greater than the length of the distal section of the outer tubular member and an inner lumen extending therein with the portion of the inner lumen within the proximal section having a diameter at least 0.002 inch greater than the inner diameter of the portion of the inner lumen within the distal section, the diameter of the inner lumen within the proximal section being about 0.01 to about 0.022 inch and the diameter of the inner lumen within the distal section being about 0.008 to 0.015 inch;

c) an inflation lumen extending between the exterior of the inner tubular member and the interior of the outer tubular member; and d) an inflatable dilatation member on the distal section of the outer tubular member having an interior in fluid communication with the inflation lumen extending between the inner and the outer tubular members.

16. The dilatation catheter of claim 15 wherein the inner diameter of the outer tubular member is about 0.002 to about 0.004 inch greater than the outer diameter of the inner tubular member.

17. The dilatation catheter of claim 15 wherein the length of the proximal section of the inner tubular member is about 1 to about 10 cm less than the proximal section of the outer tubular member.

18. An over-the-wire dilatation catheter assembly comprising:

a) an over-the-wire dilatation catheter which includes
an outer tubular member having a proximal portion with a length of at least 100 cm and an inner lumen extending therein, a distal portion with a length of at least about 15 cm and an inner lumen extending therein which has a diameter of not more than about 0.003 inch less than the minimum inner diameter of the lumen in the proximal portion;
an inner tubular member with a proximal portion having a length less than the length of the proximal portion of the outer tubular member but at least 90 cm and a distal portion with a length of at least 20 cm but greater than the length of the distal portion of the outer tubular member,
an inflation lumen extending between the inner and outer tubular members,
a guidewire receiving inner lumen extending within the inner tubular member, the portion of the guidewire receiving inner lumen within the distal section of the inner tubular member having a smaller diameter than the guidewire receiving inner lumen within the proximal section of the inner tubular member,
an inflatable dilatation member on the distal portion of the outer tubular member having an interior in fluid communication with the inflation lumen extending between the inner and the outer tubular members; and b) a guidewire slidably disposed within the guidewire receiving inner lumen within the inner tubular member of the dilatation catheter, the guidewire including
a proximal core section having a length of at least about 100 cm and a diameter between about 0.012–0.02 inch,
an intermediate core section having a diameter of at least about 0.002 inch less than the diameter of the proximal section,
a distal core section having a diameter of at least about 0.002 inch less than the diameter of the intermediate section, and
a flexible coil disposed about and secured to the distal core section and having an outer diameter not more than about 0.0015 inch greater than the diameter of the intermediate core section.

19. The over-the-wire dilatation catheter assembly of claim 18 wherein the intermediate core section of the guidewire has a length of at least 10 cm.

20. The over-the-wire dilatation catheter assembly of claim 18 wherein the distal core section has a length of at least 10 cm.

21. An angioplasty kit comprising:

a) an over-the-wire dilatation catheter which includes
an outer tubular member having a proximal portion with a length of at least about 100 cm and an inner lumen extending therein, a distal portion with a length of at least about 15 cm and an inner lumen extending therein which has a diameter of about 0.003 inch less than the minimum inner diameter of the proximal portion;
an inner tubular member with a proximal portion having a length less than the length of the proximal portion of the outer tubular member but at least about 90 cm and a distal portion with a length of at least about 20 cm but greater than the length of the distal portion of the outer tubular member,
an inflation lumen extending between the inner tubular member and the outer tubular member;
a guidewire receiving inner lumen extending within the inner tubular member with the diameter of the inner lumen in the proximal portion thereof having a larger diameter than the inner lumen extending within the distal section thereof,
an inflatable dilatation member on the distal portion having an interior in fluid communication with the inflation lumen extending between the inner and the outer tubular members; and b) a guidewire configured to be slidably disposed within the guidewire receiving inner lumen within the inner tubular member of the dilatation catheter which includes
a proximal core section having a length of at least about 100 cm and a diameter between about 0.010 and about 0.02 inch,
an intermediate core section having a diameter of at least about 0.001 inch less than the diameter of the proximal section,
a distal core section having a diameter of at least about 0.002 inch less than the diameter of the intermediate section; and
a flexible coil member disposed about and secured to the distal core section and having an outer diameter not more than about 0.0015 inch greater than the diameter of the intermediate core section.

22. The angioplasty kit of claim 21 wherein the intermediate core section of the guidewire has a length of at least 10 cm.

23. The angioplasty kit of claim 21 wherein the distal core section of the guidewire has a length of at least 10 cm.

* * * * *